US00PP30933P2

(12) United States Plant Patent
Horvath

(10) Patent No.: US PP30,933 P2
(45) Date of Patent: Oct. 8, 2019

(54) ***RUDBECKIA* PLANT NAMED 'GLITTERS LIKE GOLD'**

(50) Latin Name: ***Rudbeckia* hybrid**
Varietal Denomination: Glitters like Gold

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 15 days.

(21) Appl. No.: 15/732,772

(22) Filed: Dec. 27, 2017

(51) Int. Cl.
*A01H 5/02* (2018.01)
*A01H 6/14* (2018.01)

(52) U.S. Cl.
USPC ..... Plt./474
CPC ..... *A01H 6/14* (2018.05); *A01H 5/02* (2013.01)

(58) Field of Classification Search
USPC ..... Plt./474
CPC ..... A01H 5/02
See application file for complete search history.

(56) References Cited

PUBLICATIONS

Josiah Raymer; Grower Talks; *Rudbeckia* Production That's Anything but Rudimentary; Dec. 1, 2017; 2 pages.*

* cited by examiner

*Primary Examiner* — Kent L Bell

(57) ABSTRACT

A new and distinct variety of *Rudbeckia* plant as illustrated and described, characterized by the combination of 90 cm height, larger gold flower, and heavier bloom, compared to the seed parent.

1 Drawing Sheet

Figure 1:
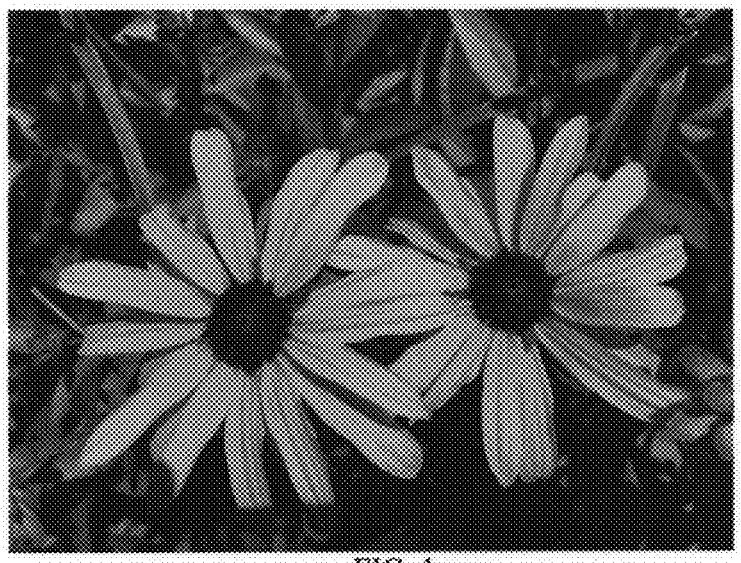

Latin name: *Rudbeckia* hybrid.
Cultivar name: 'Glitters like Gold'.

BACKGROUND OF THE INVENTION

The present invention relates to a new and distinct hybrid of *Rudbeckia* plant named 'Glitters like Gold' characterized by the combination of 90 cm height, larger gold flowers and heavier bloom, compared to the seed parent. The new *Rudbeckia* was raised as a seedling from open pollinated seed sown from the seed parent *Rudbeckia fulgida* var. *deamii*, not patented, in Hebron, Ill. in 2012. The selection of the new plant was due to its' 90 cm height, larger gold flower, and heavier bloom compared to the seed parent. Initial asexual repoduction has taken place at a nursery in Hebron, Ill. since 2015 by means of division, and stem cuttings. The new *Rudbeckia* has shown to be stable and identical in reproduction to the originally discovered plant after rooting over 600 plants from 2015 to 2017. No plants of the new *Rudbeckia* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Rudbeckia* plant named 'Glitters like Gold' characterized by the combination of 90 cm height, larger gold flower, and heavier bloom compared to the seed parent have been observed to be unique and stable. For purpose of comparison the new plant will be referred to as 'Glitters like Gold'.

Plants of the new *Rudbeckia* can be compared to plants of *Rudbeckia fulgida* var. *deamii* the seed parent, not patented. The new *Rudbeckia* plant has a mature size measuring 90 cm high and 50 cm wide while *Rudbeckia fulgida* var. *deamii* measures 120 cm high and over 60 cm wide. The new *Rudbeckia* plant has a naturally mound shaped habit while *Rudbeckia fulgida* var. *deamii* has an upright open habit. The new *Rudbeckia* plant has rounded foliage approximately 16 cm long and 6 cm wide while *Rudbeckia fulgida* var. *deamii* has foliage that reaches approximately 35 cm long and 10 cm wide.

Plants of the new *Rudbeckia* can also be compared to the *Rudbeckia fulgida* 'Early Bird Gold', patented, U.S. Plant Pat. No. 20,286. The new plant has longer foliage, 16 cm in length and soft pubescent foliage while *Rudbeckia fulgida* 'Early Bird Gold' has foliage 13-15 cm in length and rough pubescent foliage.

DESCRIPTION OF PHOTOGRAPHS

Figure 2:
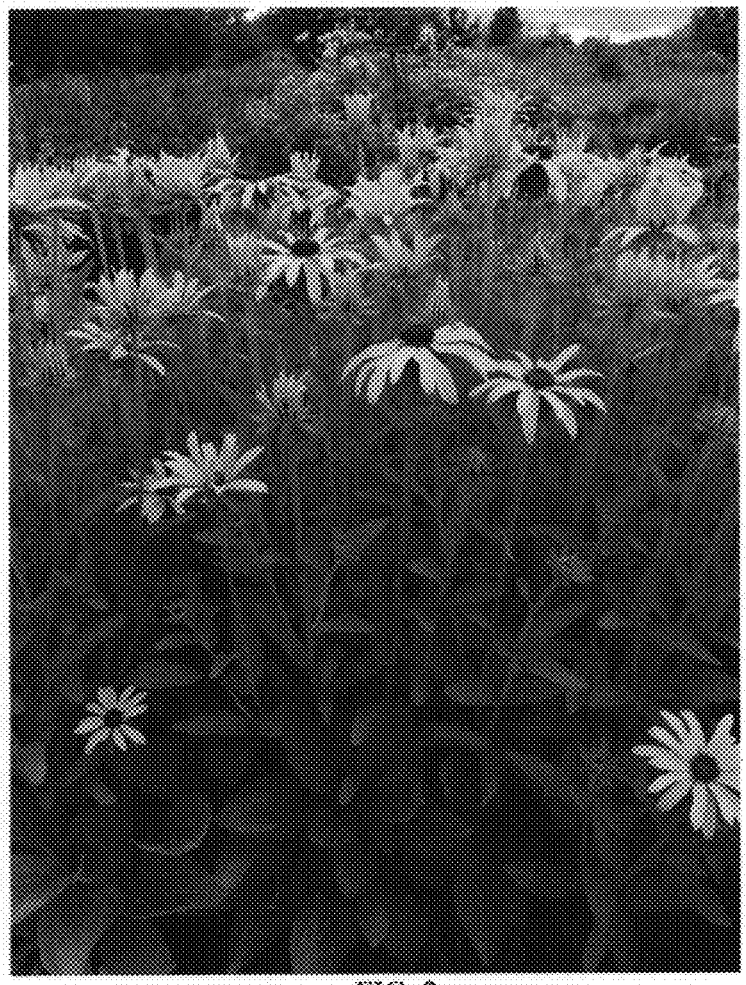

FIG. 1. A close up of the flower.
FIG. 2. A blooming 2 year old plant in July.

DETAILED BOTANICAL DESCRIPTION

In the following description, color references are made to The Royal Horticultural Society Colour Chart 2001 edition. Plants used for the description were grown for two seasons at a nursery in Hebron, Ill. Measurements and numerical values represent averages of typical plants.

Botanical classification: *Rudbeckia* cultivar Glitters like Gold.

Parentage: Male or pollen parent an unknown *Rudbeckia*, female or seed parent *Rudbeckia fulgida* var. *deamii*.

Propagation: Vegetative division and stem cutting propagation.

Root description: Fibrous, medium thickness, brown in color.

Root habit: Moderate branching, moderate density.

Plant description: Herbaceous perennial. Overall habit of the new *Rudbeckia* is a mound shaped clump, with branching stems topped by gold inflorescences starting in mid-July.

*Plant height.*—90 cm.
*Plant width.*—50 cm.
*Primary stem diameter.*—1 cm.
*Primary and secondary stem description.*—Branching, with 80 or more leaves. Leaves get smaller as they go up the stem. Strength — strong.
*Primary and lateral stem texture.*—Pubescent with hairs up to 1 mm long.
*Secondary stem description.*—Average 14 lateral stems per primary stem.
*Secondary stem length.*—28-60 cm.
*Secondary stem diameter.*—3-4 mm.
*Secondary stem internodes.*—4 cm.
*Stem color.*—146 D.

Foliage:

*Type.*—Herbaceous.
*Leaf arrangement.*—Alternate, simple, sessile.
*Length.*—16 cm.
*Width.*—6 cm.
*Shape.*—Oval.
*Apex.*—Acuminate.
*Base.*—Acute.
*Margin.*—Serrate.
*Texture.*—Pubescent, soft.
*Venation.*—Pinnate. Venation Color — 145 D.
*Adaxial leaf description.*—Color is 146 B including developing, fully expanded.
*Abaxial leaf description.*—Color is 146 C including developing, fully expanded.

Bud:

*Bud shape.*—Oblate.
*Bud length.*—9 mm.
*Bud diameter.*—22 mm.
*Bud color.*—143 B.

Inflorescence:

*Inflorescence type.*—Single, composite on branched flowering stems.
*Position.*—Borne on both terminal and axillary peduncles above the foliage.
*Number of inflorescences per plant.*—Approximately 75.
*Arrangement.*—Disc and ray florets.
*Mature center disc.*—19 mm wide and 9 mm height.
*Number of disc and ray florets.*—Approximately 300, number of ray florets 46.
*Immature disc floret color.*—145 B.
*Mature disc floret color.*—Dark brown but close to 202 A.
*Disc floret diameter.*—1 mm at apex, 1 mm at base.
*Disc floret shape.*—Rotate.
*Disc floret length.*—6-7 mm.
*Disc floret width.*—1 mm.
*Disc floret apex.*—Acute.
*Disc floret margin.*—Entire.
*Disc floret count.*—23.
*Ray floret size.*—46 mm length and 9 mm width.
*Ray floret color upon opening and in full bloom.*—Adaxial 17 A and Abaxial 17 B.
*Ray floret aspect.*—Initially incurved, then upright, then perpendicular to the peduncle.
*Ray floret shape.*—Lanceolate.
*Ray floret apex.*—Emarginate.
*Ray floret base.*—Obtuse.
*Ray floret margin.*—Entire.
*Ray floret count.*—Approximately 21 per inflorescence.
*Ray floret texture.*—Both the upper and lower surfaces are smooth, glabrous.
*Overall inflorescence size.*—10 cm across in diameter with ray florets, 1 cm in height. Receptacle height — 9 mm, diameter 2 cm across.
*Bloom period and duration.*—Mid July through mid-October. 6-8 weeks on the plant.
*Blooming habit.*—Domed, upright on 90 cm terminal flowering stems.

Phyllaries:

*Number of phyllaries per inflorescence.*—25 average.
*Length.*—13 mm.
*Width.*—4 mm.
*Shape.*—Lanceolate.
*Apex.*—Mucronate.
*Base.*—Fused.
*Margin.*—Entire.
*Texture.*—Both upper and lower surface scattered pubescence.
*Color.*—Adaxial 146 B and Abaxial 146 C.

Peduncles:

*Length of both terminal and axillary peduncles.*—44 cm.
*Diameter.*—4 mm.
*Angle.*—Erect to about 35 degrees from vertical.
*Strength.*—Strong, Texture — pubescent, Color — 146 D.

Reproductive organs:

*Androecium.*—Quantity per disc floret, 5.
*Filament length.*—5 mm.
*Filament color.*—202 A.
*Anther shape.*—Oblong.
*Anther length.*—0.5-1 mm.
*Anther color.*—12 B.
*Pollen.*—11 D color.
*Gynoecium present on ray and disc florets.*—
*Pistils.*—One, length 8 mm.
*Stigma shape.*—Two parted, Stigma color — 202 A.
*Style length.*—4 mm, Style color — 202 A.
*Scent.*—No scent noticed.

Seed and fruit: None observed.

Disease resistance: Resistance to Septoria a disease common to *Rudbeckia* has been observed on plants grown under nursery conditions.

Hardiness: Plants of the new *Rudbeckia* have been observed to be hardy to USDA Zone 5.

I claim:

1. A new and distinct variety of *Rudbeckia* plant as illustrated and described, characterized by the combination of 90 cm height, larger gold flower, and heavier bloom, compared to the seed parent.

* * * * *